(12) United States Patent
In 'T Groen et al.

(10) Patent No.: US 12,239,483 B2
(45) Date of Patent: Mar. 4, 2025

(54) ULTRASOUND TRANSDUCER UNIT WITH FRICTION GUIDING FUNCTION

(71) Applicant: KONINKLIJKE PHILIPS N.V., Eindhoven (NL)

(72) Inventors: Robertus Leonardus Maria In 'T Groen, Tilburg (NL); Fei Zuo, Eindhoven (NL); Mark Thomas Johnson, Arendonk (BE); Deep Bera, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 206 days.

(21) Appl. No.: 17/415,555

(22) PCT Filed: Dec. 12, 2019

(86) PCT No.: PCT/EP2019/084946
§ 371 (c)(1),
(2) Date: Jun. 17, 2021

(87) PCT Pub. No.: WO2020/126844
PCT Pub. Date: Jun. 25, 2020

(65) Prior Publication Data
US 2022/0054108 A1  Feb. 24, 2022

(30) Foreign Application Priority Data
Dec. 19, 2018 (EP) .................... 18213817

(51) Int. Cl.
*A61B 8/00* (2006.01)
*G06N 20/00* (2019.01)

(52) U.S. Cl.
CPC ............ *A61B 8/4254* (2013.01); *A61B 8/429* (2013.01); *A61B 8/54* (2013.01); *G06N 20/00* (2019.01)

(58) Field of Classification Search
CPC ......... A61B 8/4254; A61B 8/429; A61B 8/54; A61B 8/4245; A61B 8/461; A61B 8/42; G06N 20/00
See application file for complete search history.

(56) References Cited

U.S. PATENT DOCUMENTS

2007/0236450 A1  10/2007 Colgate
2010/0108408 A1  5/2010 Colgate
(Continued)

FOREIGN PATENT DOCUMENTS

EP  3366221 A1  8/2018
GB  1384422 A  2/1975
(Continued)

OTHER PUBLICATIONS

International Search Report and Written Opinion of PCT/EP2019/084946, dated Feb. 26, 2020.
(Continued)

*Primary Examiner* — Baisakhi Roy
*Assistant Examiner* — Kaitlyn E Sebastian

(57) ABSTRACT

An ultrasound transducer unit (12), e.g. probe, is configured with a friction guiding function. The transducer unit (12) comprises a vibration generating means (20) at a tissue contact area, and has means for sensing a sliding direction of the transducer unit across a tissue surface (42) at which the contact area is incident. The tissue surface may be an external skin surface or an internal tissue surface, e.g. in case of a catheter. A control means is operable to control the vibration of the vibration generator to adjust a level of friction at the tissue contact area. This is used by the control means to implement a friction guiding function for guiding a user in sliding the unit across the incident surface, e.g. toward a target location (44), based on controlling the friction level responsive to sensed sliding direction, for instance providing lower friction when sliding is in a target (Continued)

direction, while leaving other directions with relative higher frictional resistance.

18 Claims, 3 Drawing Sheets

(56) References Cited

U.S. PATENT DOCUMENTS

| | | | |
|---|---|---|---|
| 2014/0114193 A1* | 4/2014 | Anthony | A61B 8/429 600/459 |
| 2015/0094585 A1 | 4/2015 | Ter-Ovanesyan | |
| 2016/0119529 A1 | 4/2016 | Stolka | |
| 2017/0086785 A1* | 3/2017 | Bjaerum | A61B 8/4444 |
| 2017/0360403 A1* | 12/2017 | Rothberg | A61B 8/4427 |
| 2018/0102717 A1* | 4/2018 | Hendriks | H10N 30/802 |
| 2019/0090852 A1* | 3/2019 | Kroon | A61B 8/4245 |

FOREIGN PATENT DOCUMENTS

| | | |
|---|---|---|
| WO | 2006091494 A1 | 8/2006 |
| WO | 2015136402 A1 | 9/2015 |
| WO | 2016193131 A1 | 12/2016 |

OTHER PUBLICATIONS

Chen, H. et al "Standard Plane Localization in Fetal Ultrasound via Domain Transferred Deep Neural Networks", IEEE Journal Biomedical Health Information, vol. 19, No. 5, 2015, pp. 1627-1636.
Biet, M. et al "Implementation of Tactile Feedback by Modifying the Perceived Friction", The European Physical Journal of Applied Physics, vol. 43, 2008, pp. 123-135.

* cited by examiner

ULTRASOUND TRANSDUCER UNIT WITH FRICTION GUIDING FUNCTION

CROSS-REFERENCE TO PRIOR APPLICATIONS

This application is the U.S. National Phase application under 35 U.S.C. § 371 of International Application No. PCT/EP2019/084946, filed on Dec. 12, 2019, which claims the benefit of European Patent Application No. 18213817.2, filed on Dec. 19, 2018. These applications are hereby incorporated by reference herein.

FIELD OF THE INVENTION

The present invention relates to an ultrasound transducer unit, for example an ultrasound probe.

BACKGROUND OF THE INVENTION

Ultrasound is an important modality for medical imaging and is the primary mode of examination for investigating many pathologies.

One important area for instance is for conducting cardiovascular examination. Imaging the cardiovascular region non-invasively is most easily, directly, and accurately done using ultrasound.

A physical examination of the heart often comprises examination not only of a patient's heart, but also examination of other parts of the body including the hands, face and neck. The cardiovascular examination aims to identify any cardiovascular pathology that may be causing a patient's symptoms, such as chest pain, breathlessness, or heart failure.

Key observation which may be performed during the physical examination of the heart include: measurement of heart rate; measurement of a size of the heart (e.g. measured by percussion and feeling the ictus of the heart) for instance as an indication for enlargement of the left ventricle; and inspection of heart valve function and blood flow, for instance observed via auscultation of the heart at four standard positions, related to the different heart valves, these being the mitral valve, aortic valve, tricuspid valve, and pulmonary valve. Heart sounds and murmurs give indications for valve defects, volume overload, pressure overload and hypertrophy.

One specific form of ultrasound examination is echocardiography.

An echocardiogram is an ultrasound test which can be used for evaluating structures of the heart, as well as the direction of blood flow within the heart. Technicians specially trained in echocardiography perform the scan using an ultrasound probe to produce images and videos, often using a special probe or transducer that is placed in various places on the chest wall, to view the heart from different directions. Cardiologists, or heart specialists, are trained to evaluate the acquired images to assess heart function and provide a report of the results.

Information produced by an echocardiogram may provide indication of one or more of the following:

Heart size. Weakened or damaged heart valves, high blood pressure, or other diseases can cause the chambers of the heart to enlarge or the walls of the heart to become abnormally thickened.

Heart pumping strength. An echocardiogram can assist in determining the heart's pumping strength. Specific measurements may include a percentage of blood evacuated from a filled ventricle during each heartbeat (ejection fraction) or a volume of blood pumped by the heart in one minute (cardiac output).

Damage to the heart muscle. During an echocardiogram, it is possible to determine whether all parts of the heart wall are contributing normally to heart pumping activity. Parts that exhibit weak movement may have been damaged during a heart attack or be receiving too little oxygen. This may indicate coronary artery disease or various other conditions.

Valve problems. An echocardiogram indicates movement of heart valves as the heart beats. It can be determined from this if the valves open sufficiently wide for adequate blood flow (i.e. no stenosis) and/or close fully for preventing blood leakage (i.e. no valve regurgitation).

Heart defects. Many heart defects may be detected with an echocardiogram, including problems with heart chambers, abnormal connections between the heart and major blood vessels, and complex heart defects that may be present at birth. Echocardiograms can also be used to monitor a baby's heart development before birth.

In addition to the above, it is also possible (using more advanced analysis techniques) to assess heart wall thickness, wall kinetics and blood flow patterns.

Various different hardware implementations for ultrasound examinations exist.

The most common approach takes the form of an ultrasound probe having an array of ultrasound transducers acoustically coupled to a skin contact area located at its tip. This is slid across the patient's skin, typically using acoustic coupling gel applied between the skin and the probe. The ultrasound probe may be a handheld probe device connected to an ultrasound imaging system or device, for instance mounted in the form of a cart or trolley.

An alternative hardware approach is use of an electronic stethoscope, which assists in performing cardiac auscultation. Recent developments have been made in this area for more sophisticated processing of auscultatory heart sound signals to enable for example improved analysis and clarification of the resulting sounds, for enabling diagnosis based on the results. However, electronic stethoscopes, like traditional stethoscopes, rely on a clinician listening to auditory sounds from the heart and assessing from these sounds whether a heart is healthy or unhealthy. This is a very difficult skill and relies upon a high level of training and experience. It is vulnerable to inaccuracy.

Ultrasound by contrast is a far more intuitive examination modality, allowing it to be performed by less skilled practitioners, and rendering it less vulnerable to human error and hence unreliability. Studies have shown that, even with a limited learning period; students using ultrasound perform better assessments than experienced doctors using a stethoscope.

Ultrasound probes utilize ultrasound transducers to generate the acoustic signals. Different types of ultrasound transducer exist. The most common type of transducer are piezoelectric transducers.

One alternative, and advantageous, type are capacitive micromachined ultrasonic transducers (CMUT). CMUT transducers are a relatively recent development. CMUTs utilize changes in capacitance for providing the energy transduction function. CMUTs are constructed on silicon using micromachining techniques. A cavity is formed in a silicon substrate, and a thin membrane suspended over the cavity on which a metallized layer acts as an electrode. The silicon substrate serves as a lower electrode.

As CMUTs are micromachined devices, it is simpler using this technology to construct 2D and 3D arrays of transducers. This means large numbers of CMUTs can be included in a transducer array, providing larger bandwidth compared to other transducer technologies.

Furthermore, achieving high frequency operation is also easier using CMUTs due to their smaller dimensions. The frequency of operation depends upon the transducer cell size (in particular, the size of the cavity covered by the membrane), and also upon the stiffness of the material used for the membrane.

Furthermore, as CMUT transducers are constructed on silicon, integration of additional control or driving electronics is also easier compared to other transducer technologies. This provides the potential for reducing form factor of a device by integrating control components on the same chip as the transducers for instance.

There has recently been documented a decline in physical examination skills among physicians for example in performing manual ultrasound examination. For more experienced clinicians, this may arise due to lack of recent practice, or time constraints. Furthermore, for medical students who do demonstrate good technical ability, there are often deficiencies in clinical reasoning when conducting the exam, for instance determining which anatomical regions to examine following certain observations, or in which order. Sometimes anatomical regions are missed, when performing a scan, which are later needed for accurate diagnosis.

Challenges include knowing which anatomical regions to examine, knowing the best angles from which to examine anatomical areas and also knowing at which locations on the skin to place a probe to properly capture a particular view angle. Correct positioning of the probe on the body for capturing images is therefore a key issue.

Solutions are known for providing visual guidance for navigating a probe across the body, in particular by providing an additional screen or visual window providing instructions with text or images. However, it is very difficult and inconvenient for an operator when looking at real-time ultrasound image data (for making clinical assessments) to simultaneously follow visual probe-handling instructions.

Haptic feedback approaches are also known based on using haptic feedback devices in a probe handle for instance. These can provide some degree of non-visual guidance to a user. However, conveying directional information with current haptic solutions is very difficult, meaning some form of supplementary visual guidance is often still required.

An improved means for providing navigation guidance to an operator during ultrasound examinations is therefore sought.

SUMMARY OF THE INVENTION

The invention is defined by the claims.

According to examples in accordance with an aspect of the invention, there is provided an ultrasound transducer unit comprising:
a tissue contact area;
a vibration means at the tissue contact area;
a movement sensing means for sensing a sliding direction of the transducer unit across an incident surface; and
a controller;
the controller operable to control a slide friction of the transducer unit across an incident surface based on adjusting a vibration setting of the vibration means and the controller configured to implement a friction guiding function for guiding an operator along a particular slide path across said incident surface, the friction guiding function based on controlling the slide friction responsive to sensed sliding direction.

Embodiments of the invention are hence based on implementing frictional guidance for a user: reducing friction along a preferred direction of movement (as determined by the system) at a given moment and increasing friction (or not reducing it) in non-preferred directions.

Friction guidance is a highly efficient and direct form of guidance since it not only provides a form of haptic feedback to the user, but also physically guides or encourages the probe along the determined path. The feedback is more intuitively followed since the user can simply push the probe along the path of apparent least resistance across the surface. The solution is hence superior to mere vibrational haptic feedback which requires a user to interpret feedback signals and then judge the correct way to slide the probe.

The invention is based on application of insights surrounding the so-called stick-slip phenomenon, wherein spontaneous jerking motion can occur between two objects which are sliding over one other, i.e. situations of stick and slip occur alternately.

It is known that sticking of a sliding object can be reduced, thereby decreasing effective frictional resistance, by applying vibrations at the interface between the sliding object and the substrate or surface. The degree of sliding friction can be adjusted by controlling the oscillation amplitude or the oscillation frequency of the vibrations.

The invention applies these insights to implement a navigation or guidance function, whereby the transducer unit is guided across the surface, e.g. along a given slide path, by decreasing relative frictional resistance along the desired sliding direction. In other directions, frictional resistance may be increased, or left unaltered. This may block or impede travel in these directions while permitting or encouraging movement in the target direction.

This approach relies on knowledge of current sliding direction, and wherein, in response, the level of frictional resistance between the tissue contact area and the incident surface is configured. Friction is instantaneously increased (or kept the same) when sliding is in a wrong direction (e.g. not along a determined or known navigation path or not in a preferred navigation direction) and decreased (or kept the same) when sliding is in the correct target direction.

Using stick slip control insights to implement ultrasound navigation has not previously been considered.

The transducer unit may for example be an ultrasound probe.

The incident surface refers for instance to an incident tissue surface, e.g. skin surface. Tissue may be skin or internal tissue (for instance in the case of invasive probes such as catheters).

Controlling the slide friction for instance comprises controlling slide friction between the tissue contact area of the transducer unit and the incident surface.

The movement sensing means may also sense movement speed, i.e. sliding speed. The movement sensing means may comprise one or more accelerometers in examples.

The vibration means is for generating vibrations, in particular at the tissue contact area. The vibration setting of the vibration means may comprise at least one or more of: vibration amplitude and vibration frequency. The controller configures a slide friction level based on configuring vibration settings of the vibration means.

The guidance is friction based: increasing friction in directions not in the target direction, and reducing friction is directions in the target direction.

In examples, the tissue contact area may comprise an acoustic output area, e.g. an acoustic window. It may be acoustically coupled to one or more ultrasound transducers for generating imaging signals for example.

The controller may fully determine a guidance slide path across the incident surface in advance or such a path may be determined dynamically or iteratively, e.g. wherein only a current target sliding direction is derived at any given time, e.g. a sliding direction toward a known target location on the incident surface.

Hence, the path may be predetermined, or may emerge dynamically, for example based on real-time calculation of target sliding direction from moment to moment, for instance to navigate to a defined target location.

The controller may be configured to set a relative lower slide friction when sliding direction is in directions along the path, and set a higher slide friction when sliding direction is in directions divergent from the path.

For example, the slide friction is reduced when sliding direction is in directions along the path, and/or increased when sliding direction is in directions divergent from the path.

Higher and lower mean relative higher and lower (relative to one another).

As noted above, according to certain examples, the slide path may be dynamically determined along the length of the path.

Alternatively, the slide path may be pre-determined.

The dynamic determining of the path may be based on recurrently re-determining an instantaneous target sliding direction. This may be a direction of a most direct path to a target location for example.

According to one advantageous set of embodiments, the friction guiding function may be for guiding an operator toward a target location on said incident surface, e.g. wherein the slide path is a path toward a defined target location on said surface.

For example, based on the sensed location, a target sliding path across the incident surface to the target location may be determined, and the friction sliding function controlled for guiding the operator along said target sliding path.

The slide path may be a shortest path across said incident surface to said target location.

The shortest path may be a spatially shortest path (shortest distance path), or a temporally shortest path (shortest time). Usually these will be the same however.

The controller may determine the shortest path based on a known target location, and known or determined landscape and/or topography (e.g. map) of the incident surface. The known landscape or topology may be based on accessing a map, model or other dataset storing data representative of the landscape or topology. For example an anatomical model or map may be employed.

Alternatively, the path may be an indirect path (e.g. circuitous path), for travelling via one or more waypoints for instance, or avoiding one or more obstacles.

In examples, the ultrasound transducer unit may comprise a position sensing means. The friction guiding may be at least partially based on a sensed position of the probe on the surface. For example a target slide path for the transducer unit across the surface may be determined or calculated based on the sensed position of the probe, and based on a known target location.

In some examples, the position sensing means may facilitate or provide the movement sensing means, i.e. the movement direction may be detected via sensing change in probe position. In other examples, a separate means for sensing position may be provided. This may be a sensor or in some examples, or may be based on analysis of acquired ultrasound images, e.g. to detect anatomical landmarks.

In some examples, the friction guiding may be based at least partly on a sensed position of the probe relative to a target location, i.e. a target sliding direction is determined based on current position.

According to one or more examples, based on the sensed position, and a known target location, a current target sliding direction may be defined, and the sliding friction controlled for guiding an operator to slide the probe in said direction. The target sliding direction may for example be the direction of the shortest path to the target location.

The current target sliding direction may be recurrently updated by the controller. For example, it may be updated periodically, for instance at regular intervals. It may be updated responsive to sensed movement, or to a new sensed location.

Where position sensing is included, the position sensing at a given transducer unit location may be based on analyzing ultrasound images acquired while at said location. For example the images may be analyzed to detect anatomical landmarks which may be used to detect position of the probe.

The detection of position may be based on comparison of a current image view with a known view of a target location or region of interest. It may be based on comparison of real-time image data with a dataset or database of reference image data corresponding to different known locations across the body.

The images used for the position detection may be acquired in real-time at each given location, and analyzed in real time.

According to one set of embodiments, the controller may be configured to use a machine learning algorithm for recurrently determining a current target sliding direction. The algorithm may use ultrasound images acquired in real time as an input. The algorithm may implement image analysis of the images. The algorithm may be an algorithm trained using previous ultrasound images acquired at various locations across the incident surface, and associated location information for the images.

The vibration setting of the vibration means may comprise at least one of: a vibration amplitude of the vibration means and a vibration frequency of the vibration means.

According to one or more sets of embodiments, the vibration means may comprise one or more electroactive polymer (EAP) actuators, i.e. actuators which comprise an EAP.

Electroactive polymers (EAPs) are an emerging class of materials within the field of electrically responsive materials. EAPs can work as sensors or actuators and can easily be manufactured into various shapes allowing easy integration into a large variety of systems.

Advantages of EAPs include low power, small form factor, flexibility, noiseless operation, accuracy, the possibility of high resolution, fast response times, and cyclic actuation.

The improved performance and particular advantages of EAP material give rise to applicability to new applications.

The use of EAPs enables functions which were not possible before, or offers a significant advantage over common sensor/actuator solutions, due to the combination both of a relatively large deformation and force in a small volume or thin form factor, compared to common actuators. EAPs also give noiseless operation, accurate electronic control, fast response, and a large range of possible actuation frequencies, such as 0-1 MHz, most typically below 20 kHz.

The vibration means may additionally or alternatively comprise one or more ultrasound transducers. e.g. one or more CMUT transducers.

In further examples, the vibration means may comprise a vibration actuator, for instance a mechanical or mechatronic vibration actuator. This may include for instance an eccentric rotating mass vibrator.

Examples in accordance with a further aspect of the invention provide a method of guiding an operator of an ultrasound transducer unit in sliding the unit across an incident surface, the method comprising:

sensing a sliding direction of the transducer unit, and controlling a slide friction between the transducer unit and the incident surface responsive to the sensed sliding direction to thereby implement a friction guiding function, wherein the friction control is based on adjusting a vibration setting of a vibration means located at a tissue contact area of the ultrasound transducer unit.

Sliding direction may be sensed recurrently, e.g. periodically, e.g. at regular intervals, or responsive to sensing movement for instance (i.e. triggering of the movement sensor).

In examples, the controller may be configured to set a relative lower slide friction when sliding direction is in a target direction, and set a higher slide friction when sliding direction is divergent from the target direction.

According to an advantageous set of embodiments, the friction guiding function is configured for guiding an operator toward a target location on the incident surface. For example, the controller guides the operator along a particular path toward the target location, or in a particular direction toward the target location, for instance a most direct direction or most direct path.

The friction guiding function may be configured for guiding the operator along a shortest slide path across said incident surface to said target location.

Examples in accordance with a further aspect of the invention provide a computer program product comprising code means which, when the program is executed on a processor, the processor being operatively coupled with an ultrasound transducer unit, cause the processor to:

receive a sensor output of a movement sensing means comprised by the ultrasound transducer unit, and detect a sliding direction of the transducer unit based on the sensor output; and control a vibration setting of a vibration means located at a tissue contact area of the ultrasound transducer unit to thereby control a slide friction between the transducer unit and an incident surface, the slide friction being controlled responsive to the sensed sliding direction to thereby implement a friction guiding function.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
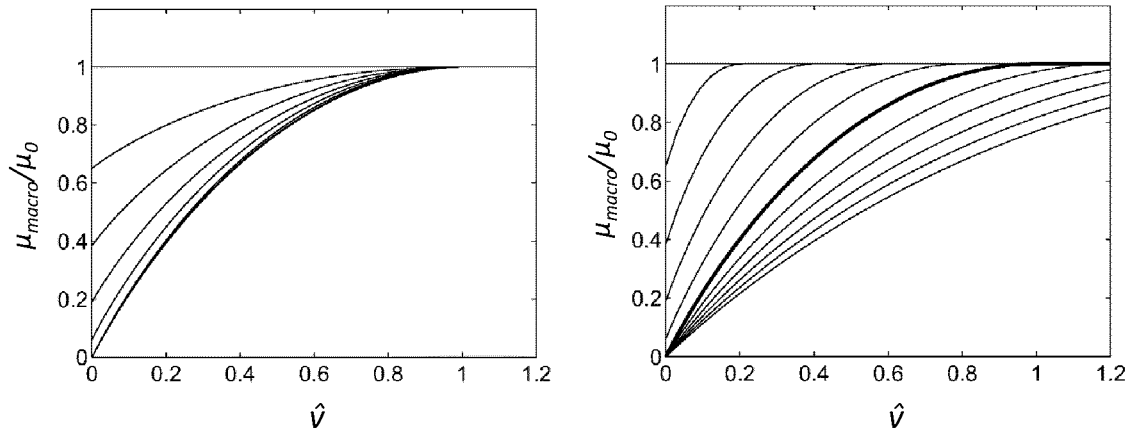
FIG. 1 shows relationships between normalized slide velocity of an object and normalized sliding friction for different vibration amplitudes.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound transducer unit, e.g. probe, configured with a friction guiding function. The transducer unit comprises a vibration generating means at a tissue contact area, and has means for sensing a sliding direction of the transducer unit across a tissue surface at which the contact area is incident. A control means is operable to control the vibration of the vibration generator to adjust a level of friction at the tissue contact area. This is used by the control means to implement a friction guiding function for guiding a user in sliding the unit across the incident surface, based on controlling the friction level responsive to sensed sliding direction, for instance providing lower friction when sliding is in a target direction, while leaving other directions with a relative higher frictional resistance.

The invention hence provides a friction guiding function for guiding, i.e. navigating, a user across said incident surface, for example toward a particular target location on the surface, along a particular path across the surface or in a particular direction or trajectory along the surface.

The friction guidance is based on controlling friction between the tissue contact surface of the ultrasound transducer unit and the surface, and this is achieved by adjusting settings of a vibration generating means at the contact surface. When the probe is sensed to be moving in a plotted target direction or path or trajectory (e.g. for reaching a target location on the surface), the vibration is adjusted to provide reduced friction. When the probe is sensed as moving contrary to the determined target direction or path or trajectory, the vibration may be adjusted to provide a relative higher degree of friction, for instance by deactivating any vibration, so that the friction with the surface is kept at its natural (higher) state.

The level of friction reduction may be adjusted dependent on a degree of deviation from the desired movement direction or path, for instance dependent on an angle of deviation. For example maximum friction reduction may be provided when movement direction is exactly parallel with the target movement direction or path, with the level of friction reduction provided (e.g. vibration amplitude or frequency) then reduced in proportion to the angle of deviation from this direction or path. When the movement is exactly opposite to the desired direction or path trajectory, the vibration level may be set at zero or minimum.

Embodiments of the invention are based on utilization of insights surrounding the stick-slip phenomenon.

The stick-slip phenomenon is a spontaneous jerking motion which can occur between two objects when sliding over each other, i.e. situations of sticking between the objects and slipping between the objects alternately occur.

In general, there are three possible stick-slip states, each yielding a different amount of instantaneous frictional resistance. One is stick (maximal frictional resistance), one is slip (less frictional resistance), and another is jump (no contact at all, where friction is zero).

Depending upon the sliding velocity and an oscillation amplitude and frequency applied at a contact surface, a specific alternation pattern of the three states may occur. At a macro level, this results in an overall effective sliding friction dependent on the ratio of occurrence of the different states.

While the jump state has lowest frictional resistance associated with it, it lacks controllability and so is not generally desirable. The slip state is the most desirable and ideally, for reduced frictional resistance, while maintaining sliding control, sliding between the two objects should be at slip state for as high a proportion of the time as possible.

The stick-slip phenomenon is associated with a critical velocity, $v_{critical}$, below which the phenomenon does not occur, or occurs with significantly reduced frequency. The critical velocity, $v_{critical}$, is dependent on vibrational amplitude, $\Delta u_z$, and vibrational frequency, $\omega$, at the interface between the objects, as well as the coefficient of friction, $\mu_0$ at the interface:

$$v_{critical} = \mu_0 \omega \Delta u_z \quad (1)$$

Hence, for a constant sliding velocity, v, effective frictional resistance can be decreased by increasing the critical velocity, $v_{critical}$, e.g. so that the critical velocity is brought above the level of the sliding velocity or raised further above it.

From equation (1) it can be seen that this can be achieved by increasing one or both of the vibrational amplitude, $\Delta u_z$, or frequency, $\omega$, at the interface between the objects.

Hence, for the present invention, reducing effective sliding friction between the tissue contact area of the ultrasound transducer unit and the incident tissue surface can be achieved by increasing the vibrational amplitude and/or frequency of the vibration means. Level of friction reduction is in general proportional to increasing vibrational amplitude and frequency.

FIG. 1 (left) shows a graph illustrating the dependency of normalized coefficient of friction at the surface interface, $\mu_{macro}/\mu_0$, (y-axis), upon normalized sliding velocity of the ultrasound transducer unit, $\hat{v} = v_{sliding}/v_{critical}$, (x-axis). The normalized sliding velocity is normalized relative to the critical velocity, $v_{critical}$, so that $\hat{v}=1$ corresponds to $\hat{v} = v_{critical}$. The normalized coefficient of friction is normalized relative to the coefficient of friction, $\mu_0$, between the contact surface of the transducer unit and the tissue surface when there is zero vibration, and sliding velocity is at the critical velocity.

Each of the graph curves or lines corresponds to a different normalized vibration amplitude, $\Delta u_z/\Delta u_{z,0}$, where $\Delta u_{z,0}$ corresponds to the absolute baseline surface height, $u_z$, level. From top to bottom the curves correspond to vibration amplitudes of $\Delta u_z/\Delta u_{z,0}=0$, 0.2, 0.4, 0.6, 0.8, 1. The upper horizontal line corresponds to $\Delta u_z/\Delta u_{z,0}=0$. It is a constant value of 1, since, at this amplitude there is no vibration, and hence $\mu_{macro}=\mu_0$, ($\mu_0$ is the coefficient of friction when vibration is zero).

It can be seen that increased oscillation amplitude decreases the effective frictional resistance (the normalized coefficient of friction) between the transducer unit and the incident surface for a given slide velocity.

The graph of FIG. 1 (left) is confined only to the slip and stick states. The graph of FIG. 1 (right) shows the same set of relationships where the jump state is also included. The lines and curves above and including the bold curve correspond, from top to bottom, to normalized oscillation amplitudes $\Delta u_z/u_{z,0}=0$, 0.2, 0.4, 0.6, 0.8, 1.0, and the curves below the bold line correspond, from top to bottom, to normalized oscillation amplitudes $\Delta u_z/u_{z,0}=1.2$, 1.4, 1.6, 1.8, 2.0.

As in the left-hand graph of FIG. 1, the upper horizontal line corresponds to $\Delta u_z/\Delta u_{z,0}=0$.

Hence, as noted above, reduced friction due to the stick-slip phenomenon may occur below the critical slide velocity:

$$\hat{v} < 1 \rightarrow v_{slide} < v_{critical} \rightarrow v_{slide} < \mu_0 \omega \Delta u_z$$

where $\hat{v} = v_{slide}/v_{critical}$, and other symbols have the same designations as set out in the paragraphs above.

In practice, applying the above theory to reduce friction places certain constraints on the range of required vibration frequencies and amplitudes, given the range of typical sliding velocities of the ultrasound probe during an examination. However, it can be calculated that the available frequencies and amplitudes of vibration using current technology are sufficient to provide for a critical velocity suitably above the typical probe sliding velocities.

For example, with application of vibration using a CMUT cell, at a vibration frequency of 2.5 MHz., and CMUT membrane oscillation amplitude of 200 nm, and with coefficient of friction $\mu_0=0.4$ (with no gel applied): $v_{critical}=0.2$ m/s.

For application of vibration with a CMUT cell at the same frequency and amplitude, and with application of gel (coefficient of friction $\mu_0=0.03$): $v_{critical}=0.015$ m/s.

In general, the typical speed of moving or sliding of an ultrasound probe during an examination is in the order of 0.05 m/s (5 cm per second). Hence, the examples above show that available vibrational amplitudes and frequencies are such as to permit control of friction in this range of slide velocities.

Hence, since the stick-slip phenomenon is dependent upon on the sliding velocity and the oscillation amplitude at the surface interface, the slide friction of an object over a surface is controllable.

Embodiments of the present invention propose to use this insight for a novel directional haptic-feedback system, guiding an ultrasound probe across a surface, for instance towards a point of interest on a human body, to support a user in finding the correct probe location without the need to either look at the probe itself or to look at separately provided visual probe-handling instructions. In particular, slide friction may be controlled such that friction reduces when sliding towards a point of interest, and increases when sliding away from a point of interest (or for instance only indirectly toward it). This induces a dynamic effect, felt when sliding the ultrasound probe. This contrasts with currently known vibro-tactile feedback, which cannot directly convey directional information.

Embodiments of the present invention, by providing direct feedback in the form of varying frictional resistance in different directions, enables directional guiding of an operator entirely non-visually, removing the need to look at probe-handling instructions. This leaves operators free to focus solely on the acquired ultrasound image information while performing the examination. The solution may be particularly beneficial for less experienced users who both benefit from the navigation guidance and also benefit from increased focus on the medical images.

Figure 2:
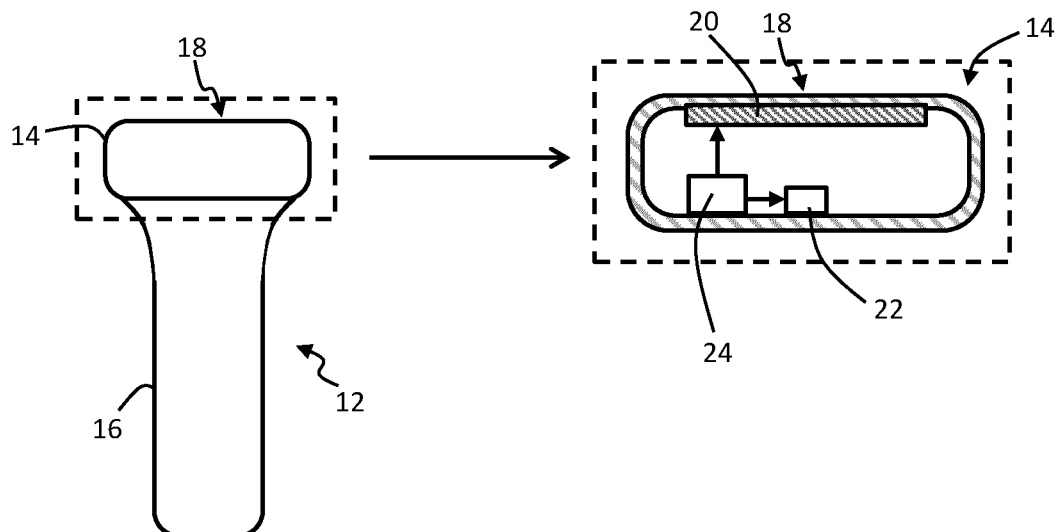
FIG. 2 schematically illustrates an example ultrasound transducer unit according to one or more embodiments.

FIG. 2 schematically illustrates an example ultrasound transducer unit according to one or more embodiments of the invention. The ultrasound transducer unit 12 is in the form of an ultrasound probe, having a probe head part 14 and a handle part 16. The right-hand side of FIG. 2 schematically depicts a cross-sectional view through the head part 14, illustrating at least a portion of its internal components.

The ultrasound transducer unit 12 comprises a tissue contact area 18, located in this example across an upper surface of the head 14. This area provides in use a contact interface with an incident surface to which the probe head is applied, so that the probe is slid across the surface via the end of the head.

A vibration means 20 is provided for generating vibrations at the tissue contact area 18. The vibration means 20 may optionally be facilitated by the ultrasound transducer elements included in the probe for generating the imaging signals. In other examples, the vibration means may be a separate dedicated component, for example a mechanical vibrator (e.g. eccentric mass vibrator), or an EAP actuator arrangement.

A movement sensing means 22 is further provided for sensing a sliding direction of the transducer unit across an incident surface. The movement sensor may comprise one or more accelerometers in some examples.

A controller 24 is further provided, operatively coupled with the vibration means 20 and the movement sensing means 22.

The controller 24 is operable to control a slide friction of the transducer unit 12 across an incident surface based on adjusting a vibration setting of the vibration means 20.

The controller is configured to implement a friction guiding function for guiding an operator across said incident surface, the friction guiding function based on controlling the slide friction responsive to sensed sliding direction.

For example, the friction guiding function guides the user along a particular slide path across the incident surface (which may be pre-determined or calculated iteratively along the path), and/or toward a target point/location on the incident surface, or in a certain trajectory across the incident surface, or according to a certain navigation route along the surface.

It is noted that the relative locations and positions of the components shown in FIG. 2 are purely schematic, and actual positions and sizes may be different. For example, although in FIG. 2, the controller 24 and motion sensing means 22 are shown as located in the head part 14 of the example probe 12, in other examples, one or both might be located in the handle part 16 of the transducer unit 12 for instance.

The ultrasound transducer unit 12 incorporates one or more ultrasound transducer elements for performing ultrasound signal generation and sensing, for example CMUT transducer elements. As noted above, in some examples, these transducer elements also facilitate the vibration means 20. Here, noise correction may be applied to correct for noise introduced in the imaging data as a result of the additional applied baseline vibration. The vibration for friction control is generally at a lower frequency than the ultrasound oscillations, meaning the vibration noise can be distinguished from the imaging signals in the data.

In use, an operator applies the ultrasound transducer unit 12 (probe in this example) to an incident tissue surface of the body. This may be an external skin surface in the case of an ultrasound probe, or may for instance be an internal tissue surface, in the case of an invasive ultrasound probe, e.g. a catheter. The user manipulates the probe over the tissue surface by sliding in the manner usually required for an ultrasound examination. Ultrasound (e.g. acoustic) settings may be adjusted on an ultrasound control unit for example, and images generated by the probe in real time monitored on a display of that control unit.

During (and preferably throughout) the examination, the controller 24 of the ultrasound transducer unit 12 implements the friction guidance function. In particular, the controller may for example recurrently determine a target sliding direction for the probe. This may be determined for guiding a user to a known target location on the tissue surface, or along a target path across the surface. The target location may be a surface location corresponding to a particular target internal anatomical location. For example, for guiding the user to an appropriate position on the tissue surface for imaging a region of the heart, such as the left ventricle by way of one example.

Figure 3:
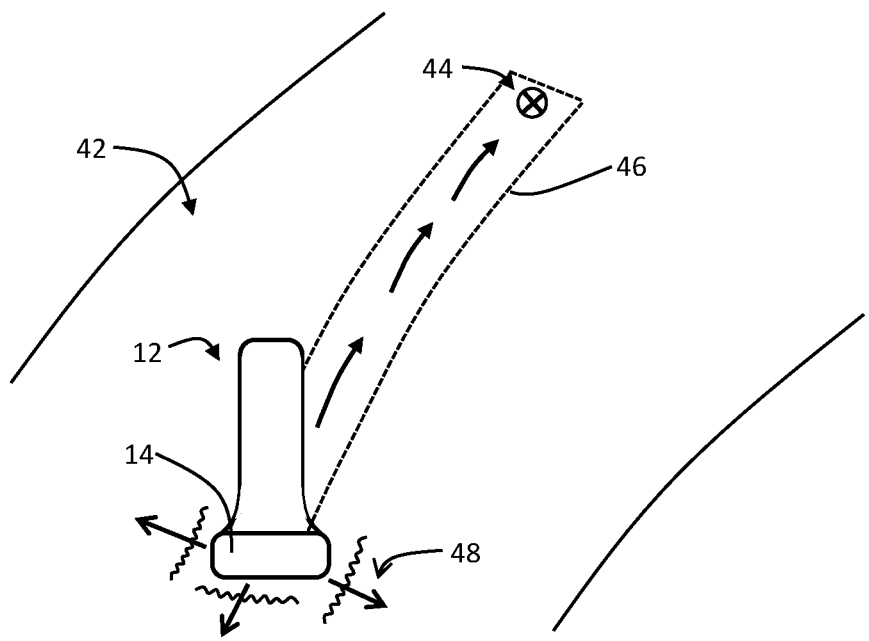
FIG. 3 illustrates an example ultrasound transducer unit in use.

FIG. 3 schematically illustrates one example ultrasound transducer unit in use according to one or more embodiments. The transducer unit 12 is shown applied to an example incident tissue surface 42, with the tissue contact area 18 at the top of the head 14 of the unit 12 applied or pressed against the tissue surface, to make sealing contact with it. Acoustic interfacing gel may be applied between the tissue contact area of the head 14 and the tissue surface in examples.

The controller 24 of the ultrasound transducer unit 12 determines an instantaneous target sliding direction for the probe, the sliding direction being along a shortest path 46 toward a target location 44 on the tissue surface 42 for the transducer unit. The controller 24 may determine the whole route of the path 46 in advance or may at any given moment determine only an instantaneous target sliding direction for the probe, representative of a most direct path to the target location. In some cases, the direction (or path) may be determined by the controller 24 for guiding the transducer unit 12 along an indirect (e.g. circuitous) path toward the location, for instance to encompass within the sliding travel route of the probe one or more way-points via which the probe travels en route to the target location 44.

Once the instantaneous target sliding direction or path 46 for the transducer unit 12 is determined by the controller 24, the controller implements the friction guidance function for guiding the probe along this direction or path, based on control of friction, responsive to sensed sliding direction.

A sliding direction of the probe 12 is determined, using the movement sensing means (e.g. an accelerometer in some examples) and this is compared with the direction of the target sliding direction or sliding path. The friction level between the probe tissue contact area 18 and the tissue surface 42 is set by the controller at a lower level responsive to sensed sliding directions along the target direction or path, and at a higher level responsive to sensed sliding directions contrary to, or divergent from, the target sliding direction or path. This is illustrated schematically in FIG. 3 which shows that for various potential sliding directions 48 divergent from the direction of the target path 46 toward target point 44, friction (represented by wavy lines) is at a higher level, leading to frictional resistance to sliding. However, along the direction of the path, sliding friction is reduced by application of vibrations using the vibration means 20 (not shown) of appropriate frequency and amplitude. This leads to a slide path along the target path 46 offering lower sliding resistance.

The higher and lower friction levels may be implemented by controlling the vibration settings of the vibration means 20 (e.g. vibration amplitude and/or vibration frequency). These are increased for increasing friction reduction, and decreased for decreasing friction reduction. Hence, experienced friction level may be negatively proportional to increasing vibration amplitude and/or frequency. In some examples, for maximum friction, no vibration is applied, or vibration is set at a minimum frequency and/or amplitude. For minimum friction, vibration may be set at a defined maximum amplitude and/or frequency.

The vibration level, and hence the level of friction reduction, may be set by the controller 24 in dependence upon the degree of alignment between sensed sliding direction (sensed using the movement detection means 22) and the direction of the instantaneous target sliding direction or path (setting a higher vibration level for closer alignment, and vice versa).

The degree of friction reduction may for instance be set in dependence upon a scalar product of a unit direction vector (i.e. normalized to magnitude 1) corresponding to the sliding direction and a unit direction vector corresponding to the target sliding direction (e.g. along the target path).

In some examples, the controller 24 may calculate the angle between the sensed current direction of motion and the desired (target) direction (the direction towards the point of interest 44). When this angle is close to zero, the controller 24 may adjust the vibration level for providing minimum sliding friction (high vibration level). When this angle is larger, the controller will adjust for providing a larger friction (e.g. reducing vibration level). When this angle is 180 degrees (i.e. opposite) to the target direction, the controller may adjust for providing maximum friction (e.g. by deactivating the vibration, or configuring the vibration settings as a minimum level).

As discussed, according to one or more sets of embodiments, the friction guidance function may be configured for guiding the ultrasound transducer unit to a target location 44 on the incident surface 42. The controller 24 may recurrently, or in response to movement for instance, determine a target sliding direction away from the current location of the probe, for reaching the target location. This may correspond for example to a direction of the most direct or shortest path across the incident surface 42 to the target location 44.

The controller 24 may be configured to determine a path across the surface to the target location, for example a shortest path. This path may be determined in advance or dynamically along the length of the path. The controller may in this example or otherwise determine at each moment a direction of the shortest path between the probe and the target location, and frictionally guide the probe in this direction. This example ultimately still results in guiding the probe along some path to the target location (if the guidance is followed to completion).

Figure 4:
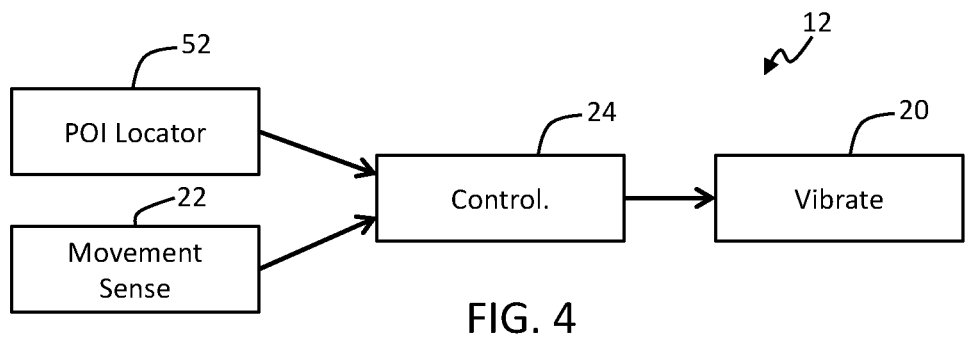
FIG. 4 shows in block diagram form a further example ultrasound transducer unit according to one or more embodiments.

FIG. 4 shows in block diagram form components of one example ultrasound transducer unit 12 according to one or more embodiments, configured for implementing frictional guidance toward a target location on the incident surface.

The unit 12 comprises a vibration means 20 ("Vibrate"), controller 24 ("Control.") and movement sensing means 22 ("Movement Sense"), as in the example of FIG. 2. The unit further comprises a target location (or point of interest) locator ("POI Locator") 52. The target location detector uses knowledge of the target location, and of the current detected motion of the transducer unit 12 relative to the target location to determine an instantaneous target movement direction for the probe. The target location detector may further generate a friction steering signal, indicative of determined target direction. This may be communicated to the controller or to the vibration means for accordingly configuring the vibration settings of the vibration means.

In particular, the signal may indicate an appropriate level of vibration for each of a set of possible movement directions, for guiding the probe in the target direction. Alternatively, the target location detector may use the detected probe instantaneous movement direction, and based on this, and the determined target location, determine an appropriate vibration setting for the vibration means 20. The vibration setting may be determined based on calculating a relative angle between the motion direction and the target direction, for instance with the vibration level set in proportion to the angle of deviation (or a normalized angle of deviation).

Although a target location detector 52 is described above as a separate component, in other examples, its functionality may be integrated in the controller 24, i.e. the controller may implement its functionality.

The ultrasound transducer unit 12 may further comprise a position detection means for determining a current location or position of the ultrasound transducer unit 12 on the target surface. This may be determined and represented as a set of co-ordinates, for instance in a local defined co-ordinate system of the incident surface, or may be represented in any other form.

Position detection may be based in some examples on a form of radio positioning, wherein the transducer unit 12 comprises means for generating and transmitting electromagnetic wave locating signals, and an external receiver unit (spaced apart from the transducer unit, at a known reference location relative to the patient or incident surface) is configured to receive the electromagnetic signals transmitted by the location means of the transducer unit. Position of the unit may be determinable based on sensed attenuation of the received signal for instance. Multiple receivers might be provided to allow for position triangulation, for instance at least three receivers. The transducer unit may instead comprise the receiver, and one or more transmitters places at various reference locations (known to the position detection means of the transducer unit) and configured to transmit locating signals for detection by the transducer unit receiver.

In some examples, position detection may be based on image analysis, in particular analysis of ultrasound image data collected in real time at each given location of the probe during use. Based on this, anatomical analysis of the image data may be applied for detecting a current location of the probe. For example, the image data is compared to a dataset of reference images or image data, labelled or tagged with corresponding location information for the images or image data. Based on a comparison, a location of the probe can be determined. Location may be determined recurrently, or each time movement is sensed for example.

According to one set of embodiments, a mapping model (for example employing a machine learning algorithm) may be used for detection of position. An example workflow based on this approach will now be briefly outlined with reference to FIG. 5.

According to this set of examples, a point of interest locator 52 (the controller 24) applies a mapping model (for instance employing a machine learning algorithm, such as a deep learning algorithm) that is configured (e.g. trained) to identify a current location of the ultrasound transducer unit 12 based on a captured local ultrasound image. Subsequently, the direction towards a given target point of interest 44 (e.g. a direction along a most direct path to the point of interest) may be determined from a determined geometric vector between the derived current location of the transducer unit 12 and the point of interest 44.

A possible work flow for determining such a geometric vector may be as set out below.

A first step comprises determining whether an image captured at the current location is within the scope of a known image view of the target region of interest, ROI, (the anatomical region which is captured in an image taken at the target navigation location 44). This is schematically illustrated in FIG. 5.

For example, an image registration algorithm may be applied for comparing the captured image view (at the current location) with the known image view associated with the target region of interest (the region beneath the target location for example). If the two do not match, or there is no detected overlap (e.g. as illustrated in FIG. 5 (left)), it is determined that the current captured view is out of view of the target location.

In other examples for instance a classifier algorithm may be employed to determine an anatomic similarity between a view captured by the ultrasound transducer unit at the current location and a view known to be associated with images at the target location (ROI).

Figure 5:
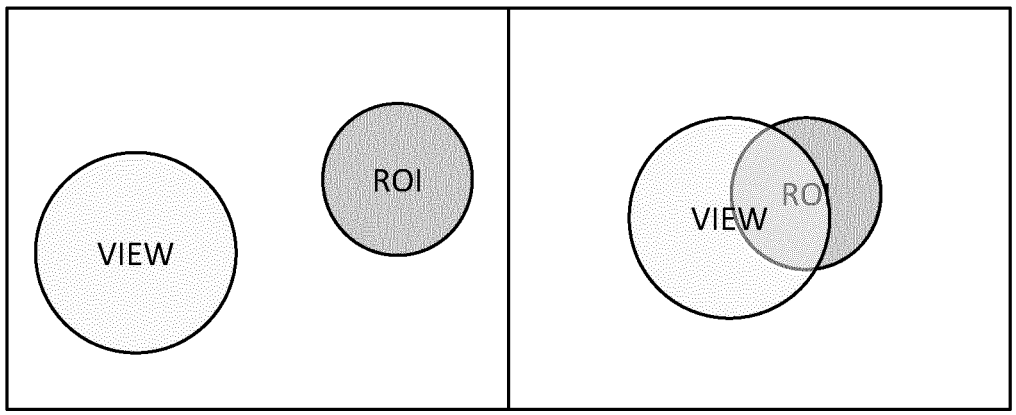
FIG. 5 illustrates a position detection means based on image registration analysis.

In the case that at least an overlap between the current view and target (ROI) view is detected (e.g. as shown in FIG. 5 (right)), only relatively small adjustments may be needed to probe position in order to arrive at the target location.

An image registration algorithm may be applied for determining a degree of registration between the current image view and target image (ROI) view (e.g. from a model database) to determine a quantitative displacement or deviation (distance+direction) to the target ROI.

In the case that there is not overlap between the current location view and the target location (ROI) view, the controller 24 may in some examples search an ultrasound atlas (comprising a dataset of known image views and their associated anatomical locations across the incident surface) for the current captured view and determine a current anatomical location of the transducer unit based on identifying a matching view in the dataset.

By way of alternative, a classifier algorithm may be employed, the algorithm trained to predict from an input current image view the current (anatomical) location. A degree of directional deviation, e.g. an angle of deviation, from the target location (ROI) view may be derived for instance using a model estimate, e.g. calculated using the set of stored view images in the atlas (dataset).

In this case, optionally a distance to the target location (ROI) may not be determined: due to the larger distance yet to travel, only a trajectory direction for travelling is immediately relevant. The controller 24 may control the vibration means in dependence upon a sensed movement direction for guiding the user in the determined target direction toward the target location (ROI).

In some examples, the mapping model for determining position from captured image data may make use of a machine learning algorithm, as noted above. The machine learning algorithm may be trained using training data comprising ultrasound images or image data representative of images captured by a transducer unit at various locations across the incident surface, each tagged with the associated location of the image. From this, the algorithm learns (is trained) to detect current location of a transducer unit based on analysis of input image data captured at that current location.

A machine-learning algorithm is any self-training algorithm that processes input data in order to produce output data. In the present case, the input data comprises ultrasound images or image data representative of images captured by a transducer unit at various locations across the incident surface, each tagged with the associated location of the image. The output data comprises an indication of current location of the transducer unit.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian model are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries in the present case may correspond to images or image data. The training output data entries may be the anatomical location to which each image corresponds.

By way of non-limiting example, one example machine learning algorithm that may be employed in embodiments of the present invention is outlined in detail in the paper: Standard Plane Localization in Fetal Ultrasound via Domain Transferred Deep Neural Networks, Chen H, Ni D, Qin J, Li S, Yang X, Wang T, Heng P A, IEEE J Biomed Health Inform. 2015 September; 19(5):1627-36.

This paper describes a deep learning based framework for detecting standard viewing planes for fetal ultrasound. The same deep learning approach might be applied, with suitable adaptations, for probe location detection using ultrasound images, as discussed above.

The ultrasound transducer unit of the invention comprises a motion sensing means 22. Different options are possible for implementing the motion sensing means 22 of the ultrasound transducer unit 12.

According to one or more examples, the motion sensing means comprises an accelerometer. Accelerometers are otherwise known as G-sensors.

An accelerometer can measure movement of an object (via sensing acceleration forces of the object), generally in three dimensions. More generally, accelerometers are able to sense tilt (attitude), acceleration, vibration and impact forces. For example, in other fields, a mobile device typically may use its accelerometer to determine its current orientation, in order to rotate the screen to match. A wearable fitness device may measure distance, number of steps taken and pace of movement. Gaming devices often use accelerometer input to measure tilt and/or rotation of the gaming handset in order to control the onscreen action.

According to one or more examples, the motion sensing means may comprise a magnetic sensor, or eCompass. Such sensors detect device heading based on the Earth's magnetic field. Many consumer devices on the market incorporate magnetic sensors to enable accurate directional pointing for map orientation and navigation applications.

Magnetic sensors are also able to provide accurate position determination.

GPS can also provide position information. However, while GPS provides accurate location detection in outdoor environments, given current technology limits, it is generally not available indoors and often only sporadically available in dense urban areas. Magnetic sensors by contrast support dead reckoning, wherein a device position may be tracked based on sensed movement direction and based on the last known position (e.g. a known reference location or starting location), enabling accurate positioning indoors and in GPS-challenged areas.

According to one or more examples, the movement sensing means may comprise one or more gyroscopes. A gyroscope may measure rotation rate of a device. This may be used for instance for measuring tilt or attitude of the ultrasound transducer unit.

Any other form of movement sensor may additionally or alternatively be used, and the above examples are not limiting. One or more of the above outlined options may also be combined according to one or more examples, so that an ultrasound transducer unit 12 comprises a combination of the above example motion sensing means.

As noted above, the ultrasound transducer device comprises one or more ultrasound transducer elements for generating and sensing the ultrasound acoustic signals for performing imaging. An ultrasound transducer array may in advantageous examples be included, for instance having beam steering functionality based on applying appropriate delays to pulse firings of the array of elements. This can be controlled by a beam steering controller. The skilled person will be aware of means for implementing ultrasound transducer elements and arrays for implementing ultrasound imaging.

According to one or more sets of advantageous embodiments, the ultrasound transducer elements used for imaging may also be employed for facilitating the vibration means 20. To implement vibration at a particular level, the controller 24 may be configured to apply to the whole set of ultrasound transducer elements or a subset of the elements a consistent baseline oscillatory signal of a frequency matching the desired vibration frequency. Any ultrasound signals are generated by applying ultrasound frequency drive signals on top of, or superposed with, the baseline vibration signal.

For example, typically, the generated vibrations will have a much lower frequency than the ultrasound acoustic signals. Hence these two signals do not significantly interfere with one another, even when generated using the same transducer component. Hence a single set of transducer elements can be driven, where necessary, to generate both vibration signals and ultrasound imaging signals simultaneously. Sensing of reflected ultrasound signals is also possible simultaneously with vibration generation, since, again, the disparity in the frequencies of the two kinds of signal mean that the two can be easily distinguished and separated from one another, for instance using a high pass filter to pass only the (higher frequency) imaging signals.

In some cases, the generated vibrations may have a higher frequency than the generated ultrasound imaging signals. For example, it is generally preferable for the vibration to have a maximal value of [vibration amplitude]*[frequency] (in order to achieve maximal friction reduction). If the transducer has the same available maximum amplitude for all frequency levels, then it may be preferable to make the vibrations of a higher frequency than the imaging signals.

In either case, the frequencies of the two kinds of signal are typically sufficiently distinct from one another to avoid significant interference between the two.

When the ultrasound transducer elements are driven for generating the (friction reducing) vibrations, the imaging capability may be slightly reduced due to the vibration noise. During the navigation of the probe to the target point of interest 44 on the incident surface, detailed imaging of the anatomy beneath the surface is not required (since the desired imaging location is not yet reached), and hence the reduced imaging capability does not in general pose a significant difficulty. However, the additional noise may be overcome, according to one or more examples, by controlling the transducer elements with alternating imaging and vibration (oscillator) modes.

The ultrasound transducer elements may take any suitable form. The transducer elements may include piezoelectric transducers, e.g. Piezoelectric Micromachined Ultrasonic transducers (PMUT) and/or capacitive transducers, e.g. Capacitive Micromachined Ultrasonic transducers (CMUT).

According to one advantageous set of embodiments, the ultrasound transducer unit may include an attitude sensing means for determining an attitude (i.e. tilt angle) of the probe, for instance relative to the incident surface. This functionality may be facilitated by the movement detection means in some examples, for instance where the movement detection means comprises one or more accelerometers and/or gyroscopes.

Detection of attitude of the ultrasound transducer unit 12 enables the vibrational direction guidance to be further augmented with tilt guidance, for guiding a user in obtaining a particular view of the imaged object or region.

The controller 24 may access a dataset (locally or remotely stored) comprising a set of target tilt angles or attitudes for the ultrasound transducer unit 12 associated within different anatomical locations and for imaging different anatomical features or bodies. The controller may determine based on reference to the dataset a target attitude for the ultrasound transducer unit 12 based on a current location of the probe on the body and/or one or more user input commands indicating a desired anatomical object or view (e.g. view angle) which is to be captured.

The motion sensing means or separate dedicated tilt sensor may sense a current transducer unit 12 attitude and compare this with the identified target attitude for the transducer unit. Based on this, the controller 24 may determine a required tilt translation of the transducer unit from the current attitude in order to arrive at the target attitude. This may be determined as a geometric translation vector necessary to arrive at the target tilt position.

This may be performed for instance using a scalar product calculation between a direction vector corresponding to the current probe attitude and a vector corresponding to the target probe attitude. This allows determination of an angular deviation between the two vectors based for instance on the standard formula $\theta = \arccos((a \cdot b)/(|a||b|))$, where a and b represent the two direction vectors.

Since tilt angle or attitude is fully represented only by a three-dimensional vector, determining required angular translation may performed in two steps, for instance by representing each attitude (current and target) with a pair of two-dimensional vectors, one in the horizontal plane (representing horizontal rotation) and one in the vertical plane (representing vertical rotation). A necessary rotational translation for arriving at the target attitude may then be determined in two parts as a horizontal rotation and vertical rotation based on use of corresponding scalar products of the horizontal vectors of the current and target attitudes and of the vertical vectors.

To guide an operator to the target attitude, haptic feedback may be provided to the operator. In some examples, a torque feedback device may be incorporated in the ultrasound transducer unit 12, for instance in a handle part of the unit. A torque feedback device is capable of providing an oppositional force feedback to an applied turning force. This can be utilized in the present case for instance to apply an opposing force when the transducer unit is tilted in a direction counter to, or divergent to, the determined translation vector or angle for achieving the target attitude. However, when the operator tilts in the correct translation angle or vector, no oppositional force may be applied. This provides a direct counter-force feedback against incorrect tilt angles, similar to the direct frictional resistance feedback generated by the vibration means for guiding correct sliding direction across the surface.

The invention includes a vibration means. As discussed above, the vibration means may in certain embodiments be facilitated by the ultrasound transducer elements used for ultrasound imaging. The same elements may be used both for generating the vibration and for generating the ultrasound signals, where the two may be generated by the same elements simultaneously or by alternating between vibration and ultrasound modes. Where vibration and ultrasound signals are generated by the same elements simultaneously, signal processing may be applied to received reflection signals to filter signal parts associated with the frictional vibrations (e.g. a low or high pass filter). Noise correction may additionally or alternatively be applied to counter noise generated in the reflection signals by the vibration. In some examples, the vibration control signal may be used as an input to the signal processing for use in selecting or filtering the signal parts associated with the vibration.

In other examples, one subset of transducer elements may be used solely for imaging and another used solely for generating the vibrations. Noise correction may also be applied to received signals in this example since the reflected signals may still comprise noise components due to the local vibration.

In some examples, a separate vibration means 20 (separate to the ultrasound transducers) may be provided. Different options are possible for implementing a separate vibration means 20.

According to one or more examples, one or more mechanical or mechatronic vibrators may be provided.

In some examples, the vibration means may comprise one or more linear resonant actuators.

In some examples, the vibration means may comprise one or more eccentric rotating mass vibration motors.

One or more of these above examples may be combined in various examples.

According to one set of embodiments, the vibration means may comprise one or more responsive material actuators for generating the vibrations.

One example is use of one or more electroactive polymer actuators. Such actuators may include one or more layers or bodies of electroactive polymer material, with electrodes for electrically stimulating deformation of the material, to thereby provide the actuation effect. Driving these in a periodic driving scheme generates oscillatory or vibratory actuation output.

Electroactive polymers (EAPs) are an emerging class of materials within the field of electrically responsive materials. EAPs can work as sensors or actuators and can easily be manufactured into various shapes allowing easy integration into a large variety of systems.

Materials have been developed with characteristics such as actuation stress and strain which have improved significantly over the last ten years. Advantages of EAPs include low power, small form factor, flexibility, noiseless operation, accuracy, the possibility of high resolution, fast response times, and cyclic actuation.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (tens of megavolts per meter) but low currents. Polymer layers are usually thin to keep the driving voltage as low as possible.

Ionic EAPs are activated by an electrically induced transport of ions and/or solvent. They usually require low voltages but high currents. They require a liquid/gel electrolyte medium (although some material systems can also operate using solid electrolytes).

Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimensionwise). The electrolyte can be a liquid, a gel or a solid material (i.e. complex of high molecular weight polymers and metal salts). Most common conjugated polymers are polypyrrole (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Figure 6:
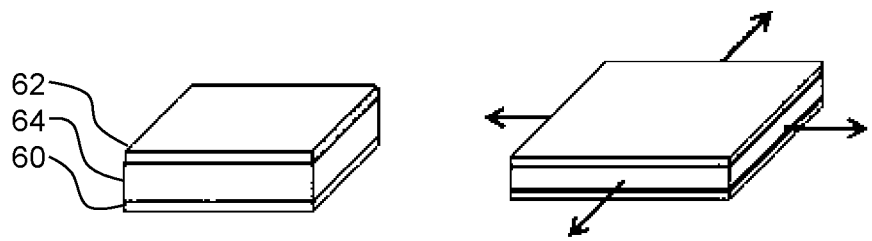
FIG. 6 shows a known electroactive polymer (EAP) device which is not clamped.
Figure 7:
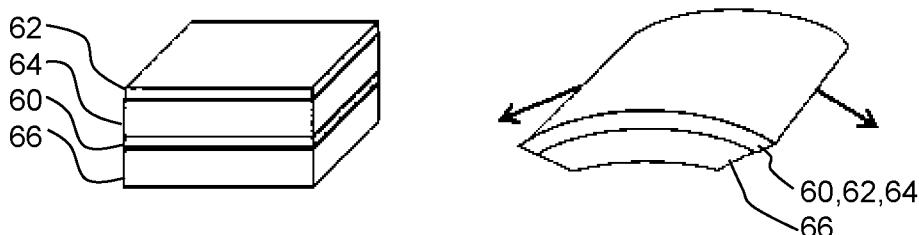
FIG. 7 shows a known electroactive polymer device which is constrained by a backing layer.

FIG. 6 and FIG. 7 show two possible operating modes for an EAP device.

The device comprises an electroactive polymer layer 64 sandwiched between electrodes 60, 62 on opposite sides of the electroactive polymer layer 64.

FIG. 6 shows a device which is not clamped. A voltage is used to cause the electroactive polymer layer to expand in all directions as shown.

FIG. 7 shows a device which is designed so that the expansion arises only in one direction. The device is supported by a carrier layer 66. A voltage is used to cause the electroactive polymer layer to curve or bow.

Together, the electrodes, electroactive polymer layer, and carrier may be considered to constitute the overall electroactive polymer structure.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

For the purposes of the present invention, the vibration means 20 may be facilitated by providing electro-active polymer actuators in vibrational communication with the tissue contact area 18 of the ultrasound transducer unit 12. These may be driven with an alternating (oscillatory) drive signal (electrical stimulation) provided at a frequency matching the desired vibration frequency. The response time of EAPs is sufficient to enable even MHz. frequency vibration. For field-driven EAPs, the drive signal may take the form of an (alternating) electric field applied between opposed electrodes sandwiching one or more layers or bodies of EAP material. For ionic EAPs, the drive signal may take the form of an applied (alternating) current. In a simple embodiment, the vibration may be created by alternately actuating the EAP (e.g. at voltage V=150 Volts) and de-actuating the EAP (V=0 Volts)

EAP actuators are ideal for the embodiments of the present invention due to their very thin form factor (<<1 mm), and the ability to shape them to any desired footprint. They are also highly flexible, permitting their application to curved surfaces. Even at very small sizes, they are capable of actuating at frequencies in the order of 1000 Hz and above, and with amplitude of around 1 mm. As described in the examples above, these frequencies and amplitudes are sufficient to move between a high friction situation (without actuation) and a low friction situation (with actuation) at typical probe sliding speeds.

Note that for friction reduction, it is the product of the frequency and amplitude of the vibrations which is generally important for determining the degree of friction reduction provided by the vibration. Hence a vibration having a lower frequency with higher amplitude may provide the same friction reduction effect as a vibration with a higher frequency but lower amplitude.

One example EAP actuator drive scheme comprises driving the EAP actuators with combined signals comprised of a DC signal component and a superposed high frequency AC signal component. This results in generation of surface vibrations which are superposed atop a baseline actuator displacement. The baseline actuator displacement can be configured such as to lift the tissue contact surface at least partially away from the incident surface, such that the majority of the contact-surface is no longer in contact with the incident surface: only the EAP actuator(s) is in contact. This hence reduces the total contact area with the incident surface ("floating contact"), which greatly reduces the friction.

The AC ripple signal atop the DC baseline signal provides the vibratory friction reduction in addition. It may also loosen trapped particles or mechanically interlocked surface defects (e.g. local surface roughness peaks or scratches). This further reduces effective sliding friction between the tissue contact surface 18 and the incident surface.

The lifting of the contact surface may be such as to lift the ultrasound imaging transducers away from the incident surface when the DC signal is applied. Where imaging is not used for the probe slide navigation over the surface, this is advantageous, since it further reduces contact friction. Where imaging is used to guide navigation across the surface, the EAP actuators may be configured such that the DC baseline signal lifting does not lift the imaging actuators away from contact with the incident surface.

Figure 8:
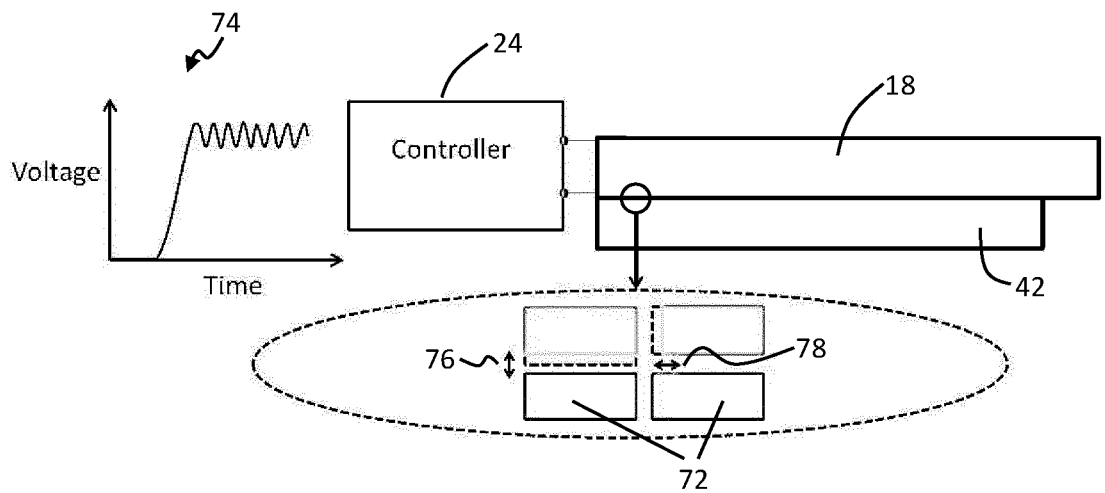
FIG. 8 illustrates use of EAP actuators for generating vibrations in an example ultrasound transducer unit according to one or more embodiments.

FIG. 8 schematically illustrates a cross-sectional view of an example tissue contact area 18 applied to an incident tissue surface 42, the tissue contact area 18 comprising a set of EAP actuator elements 74 disposed at its surface. These are illustrated in the oval beneath the two illustrated surface layers. The waveform of an example applied signal is shown in the schematic graph 74, where the y-axis represents voltage, and the x-axis represents time. The drive signal applied by the controller 24 comprises an AC (ripple) signal superposed atop a DC baseline driving signal. The resulting surface vibrations provide anti-stick properties.

The EAP actuator elements 72 are configured such that the drive signal 74 generates both normally oriented 76 and laterally oriented 78 vibrations. The two orientations of actuation may be achieved using two different subsets of actuation elements. The two subsets may each be clamped in a different configuration for inducing the different directional vibrations. Normal vibrations can be achieved by clamping the EAP layer between its side surfaces. Lateral vibrations may be achieved by clamping the layer between its upper and lower surfaces.

The EAP actuator elements 72 may each comprise a single layer of EAP or a multilayer EAP stack. The EAP actuator may in some examples comprise a bending actuator. In this configuration, the EAP layer is clamped at only one end, leaving the other end free to bend. This free end oscillates up and down in response to an alternating drive signal (or side to side, depending upon installation orientation).

In general, the higher the amplitude of the AC signal, the lower will be the experienced slide friction (as the vibrations are larger).

Examples in accordance with a further aspect of the invention provide a method of guiding an operator of an ultrasound transducer unit in sliding the unit across an incident surface.

The method comprises:
sensing a sliding direction of the transducer unit, and
controlling a slide friction between the transducer unit and the incident surface responsive to the sensed sliding direction to thereby implement a friction guidance function, wherein the friction control is based on adjusting a vibration setting of a vibration means located at a tissue contact area of the ultrasound transducer unit.

For example, the friction guiding function may be for guiding the operator along a particular slide path, or in a particular slide trajectory, and/or for guiding the operator toward a target location on the incident surface.

The controller may be configured to set a relative lower slide friction when sliding direction is in a target direction, and set a higher slide friction when sliding direction is divergent from the target direction.

As noted, the friction guiding function in some examples may be for guiding an operator toward a target location on said incident surface.

The friction guiding function may be for guiding the operator along a shortest slide path across said incident surface to said target location.

Implementation options and details for each of the above steps may be understood and interpreted in accordance with the explanations and descriptions provided above for the apparatus aspect of the present invention (i.e. the transducer unit 12 aspect).

Any of the examples, options or embodiment features or details described above in respect of the apparatus aspect of this invention (in respect of the transducer unit 12) may be applied or combined or incorporated mutatis mutandis into the present method aspect of the invention.

Examples in accordance with a further aspect of the invention provide a computer program product comprising code means which, when the program is executed on a processor, the processor being operatively coupled with an ultrasound transducer unit, cause the processor to:

receive a sensor output of a movement sensing means comprised by the ultrasound transducer unit, and detect a sliding direction of the transducer unit based on the sensor output; and control a vibration setting of a vibration means located at a tissue contact area of the ultrasound transducer unit to thereby control a slide friction between the transducer unit and an incident surface, the slide friction being controlled responsive to the sensed sliding direction to thereby implement a friction guiding function.

As discussed above, certain embodiments make use of electroactive polymers (EAPs). Materials suitable for the EAP component are known. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP component of each unit may be sandwiched between electrodes. The electrodes may be stretchable so that they follow the deformation of the EAP material. Materials suitable for the electrodes are also known, and may for example be selected from the group consisting of thin metal films, such as gold, copper, or aluminum or organic conductors such as carbon black, carbon nanotubes, graphene, poly-aniline (PANT), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An ultrasound transducer unit, comprising:
   a tissue contact area;
   a vibration generator at the tissue contact area;
   a movement sensor for sensing a sliding direction of the ultrasound transducer unit across an incident surface; and
   a controller operable to control a slide friction of the ultrasound transducer unit across an incident surface based on adjusting a vibration setting of the vibration generator, and configured to implement a friction guiding function for guiding an operator along a slide path across the incident surface based on controlling the slide friction responsive to a sensed sliding direction, wherein the controller is configured to set a relative lower slide friction by increasing the vibration setting when the sliding direction is along the slide path, and set a higher slide friction by decreasing the vibration setting when the sliding direction is divergent from the slide path.

2. An ultrasound transducer unit as claimed in claim 1, wherein
   the slide path is dynamically determined along a length of the slide path.

3. An ultrasound transducer unit as claimed in claim 1, wherein the friction guiding function is for guiding an operator toward a target location on the incident surface.

4. An ultrasound transducer unit as claimed in claim 3, wherein the slide path is a shortest path across the incident surface to the target location.

5. An ultrasound transducer unit as claimed in claim 1, wherein the ultrasound transducer unit comprises a position sensor, and wherein the friction guiding is at least partially based on a sensed position of the ultrasound transducer unit on the incident surface.

6. An ultrasound transducer unit as claimed in claim 5, wherein
   based on the sensed position, and a known target location, a current target sliding direction is defined, and the sliding friction is controlled for guiding an operator to slide the ultrasound transducer unit in the direction.

7. An ultrasound transducer unit as claimed in claim 5, wherein position sensing by the position sensor at a given location of the ultrasound transducer unit is based on analyzing ultrasound images acquired at the given location.

8. An ultrasound transducer unit as claimed in claim 1, wherein the controller is configured to apply a machine learning algorithm for recurrently determining a current target sliding direction, the algorithm using ultrasound images acquired in real time as an input, and
   preferably wherein the algorithm is an algorithm trained using previous ultrasound images acquired at various locations across the incident surface, and associated location information for each image.

9. An ultrasound transducer unit as claimed in claim 1, wherein the vibration setting comprises at least one of: a vibration amplitude of the vibration generator and a vibration frequency of the vibration generator.

10. An ultrasound transducer unit as claimed in claim 1, wherein the vibration generator comprises one or more electroactive polymer actuators; and/or the vibration generator comprises one or more ultrasound transducers.

11. A ultrasound transducer unit as claimed in claim 1, wherein the slide path is pre-determined.

12. A method of guiding an operator of an ultrasound transducer unit in sliding the ultrasound transducer unit across an incident surface, the method comprising:

sensing a sliding direction of the ultrasound transducer unit, and controlling, by a controller, a slide friction between the ultrasound transducer unit and the incident surface responsive to the sensed sliding direction to thereby implement a friction guiding function, wherein controlling the slide friction is based on adjusting a vibration setting of a vibration generator located at a tissue contact area of the ultrasound transducer unit, wherein the controller is configured to set a relative lower slide friction by increasing the vibration setting when the sliding direction is along the slide path, and set a higher slide friction by decreasing the vibration setting when the sliding direction is divergent from the slide path.

13. A method as claimed in claim 12, wherein the friction guiding function is for guiding an operator toward a target location on the incident surface.

14. A method as claimed in claim 12, wherein the sliding direction is dynamically determined.

15. A method as claimed in claim 12, wherein the sliding direction is pre-determined.

16. A tangible non-transitory computer readable storage medium that stores a computer program, wherein the computer program, when executed by a processor, causes the processor to:

receive a sensor output of a movement sensor comprised by an ultrasound transducer unit, and detect a sliding direction of the ultrasound transducer unit based on the sensor output; and control a vibration setting of a vibration generator located at a tissue contact area of the ultrasound transducer unit to thereby control a slide friction between the ultrasound transducer unit and an incident surface, the slide friction being controlled responsive to the detected sliding direction to thereby implement a friction guiding function, wherein the controller is configured to set a relative lower slide friction by increasing the vibration setting when the sliding direction is along the slide path, and set a higher slide friction by decreasing the vibration setting when the sliding direction is divergent from the slide path.

17. A tangible non-transitory computer readable storage medium as claimed in claim 16, wherein the sliding direction is dynamically determined.

18. A tangible non-transitory computer readable storage medium as claimed in claim 16, wherein the sliding direction is pre-determined.

* * * * *